(12) United States Patent
Dickhans (10) Patent No.: US 12,232,768 B2
(45) Date of Patent: Feb. 25, 2025

(54) CANNULA FOR PREVENTING TUMOR SEEDING

(71) Applicant: Covidien LP, Mansfield, MA (US)

(72) Inventor: William J. Dickhans, Longmont, CO (US)

(73) Assignee: Covidien LP, Mansfield, MA (US)

( * ) Notice: Subject to any disclaimer, the term of this patent is extended or adjusted under 35 U.S.C. 154(b) by 473 days.

(21) Appl. No.: 17/631,685

(22) PCT Filed: Jun. 12, 2020

(86) PCT No.: PCT/US2020/037400
§ 371 (c)(1),
(2) Date: Jan. 31, 2022

(87) PCT Pub. No.: WO2021/029955
PCT Pub. Date: Feb. 18, 2021

(65) Prior Publication Data
US 2022/0273339 A1    Sep. 1, 2022

Related U.S. Application Data

(60) Provisional application No. 62/885,366, filed on Aug. 12, 2019.

(51) Int. Cl.
*A61B 17/34* (2006.01)
*A61B 10/02* (2006.01)
*A61B 17/00* (2006.01)

(52) U.S. Cl.
CPC ...... *A61B 17/3431* (2013.01); *A61B 10/0233* (2013.01); *A61B 2017/00367* (2013.01)

(58) Field of Classification Search
CPC ............ A61B 17/3431; A61B 10/0233; A61B 2017/00367; A61B 2017/3435
See application file for complete search history.

(56) References Cited

U.S. PATENT DOCUMENTS

| 5,848,978 | A | 12/1998 | Cecchi |
| 6,344,026 | B1 | 2/2002 | Burbank et al. |
| 9,282,993 | B1 * | 3/2016 | Cohen ................ A61B 17/3421 |

(Continued)

FOREIGN PATENT DOCUMENTS

| WO | 9733520 A1 | 9/1997 |
| WO | 2012123879 A1 | 9/2012 |
| WO | 2014121207 A1 | 8/2014 |

OTHER PUBLICATIONS

International Search Report and Written Opinion dated Sep. 1, 2020, issued in corresponding international appln. No. PCT/US2020/037400, 8 pages.

*Primary Examiner* — Tan-Uyen T Ho
*Assistant Examiner* — Cherie M Poland
(74) *Attorney, Agent, or Firm* — Carter, DeLuca & Farrell LLP (57) ABSTRACT

A cannula for use in a surgical procedure includes a tubular shaft and a tether coupled to a distal end portion of the tubular shaft. The distal end portion of the tubular shaft is configured to turn inside out in response to a threshold proximally-oriented force applied to the tether. Sections of the distal end portion may break apart or separate from one another about a groove formed in the tubular shaft.

13 Claims, 6 Drawing Sheets

(56) References Cited

U.S. PATENT DOCUMENTS

2014/0018823 A1* 1/2014 Steger .................... A61B 34/70
606/130
2015/0073299 A1* 3/2015 Vetter ................ A61B 10/0266
600/564

* cited by examiner

CANNULA FOR PREVENTING TUMOR SEEDING

CROSS-REFERENCE TO RELATED APPLICATION

This application claims benefit of and priority to U.S. Provisional Application No. 62/885,366, filed Aug. 12, 2019, which is incorporated herein by reference in its entirety.

FIELD

The present technology is related generally to a cannula that prevents tumor seeding during surgical procedures.

BACKGROUND

Tumor or neoplastic seeding is the local implantation of tumor cells caused, e.g., by medical instruments that have been contaminated during their removal from a tumor site. This phenomenon may occur, for example, in laparoscopic surgical procedures or during tissue biopsies. When using a needle to examine, separate, or extract tumors, needle-tract seeding may occur, which is the implantation of neoplastic cells along the instrument insertion tract into the tissue of the patient.

SUMMARY

In one aspect, the present disclosure provides a cannula for use in a surgical procedure. The cannula includes a tubular shaft having a distal end portion, a first groove extending longitudinally along the distal end portion of the tubular shaft, and a first tether coupled to the distal end portion of the tubular shaft. The distal end portion is configured to break or bend about the first groove in response to a threshold proximally-oriented force applied to the first tether to evert the distal end portion of the tubular shaft.

In aspects, the at least one tether may include a first tether coupled to a first longitudinal section of the distal end portion of the tubular shaft, and a second tether coupled to a second longitudinal section of the distal end portion of the tubular shaft.

In aspects, the tubular shaft may be fabricated from a plastic.

In aspects, the plastic may be a high temperature plastic.

In aspects, the plastic may be polyetheretherketone, polyetherimide, polysulfone, and/or polyvinylidene fluoride.

In aspects, the tubular shaft may define a second groove circumferentially about the distal end portion of the tubular shaft.

In aspects, the first groove may extend parallel with a longitudinal axis defined by the tubular shaft.

In aspects, the first groove may be a pair of grooves disposed on opposite sides of the distal end portion of the tubular shaft.

In aspects, the distal end portion of the tubular shaft may include a first longitudinal section and a second longitudinal section. The first and second longitudinal sections may be configured to separate from one another about the pair of grooves and fold inwardly.

BRIEF DESCRIPTION OF THE DRAWINGS

Objects and features of the presently disclosed cannula will become apparent to those of ordinary skill in the art when descriptions of various embodiments thereof are read with reference to the accompanying drawings, of which.

DETAILED DESCRIPTION

The disclosure is generally directed to a cannula having a distal region that is selectively separable from the remainder of the cannula and configured to be drawn into the interior of the cannula. During procedures where the distal region of the cannula may contact cancerous cells, the distal region may be separated and/or torn and withdrawn into the cannula to prevent the potentially contaminated distal region of the cannula from tract seeding. These and other aspects of the present disclosure are described in greater detail below.

Although the cannula and methods of using the cannula are described below with reference to a biopsy procedure, the cannula may also be used for other minimally invasive procedures, such as, for example, the cannula may be used as an access cannula during an ablation procedure.

Figure 1:
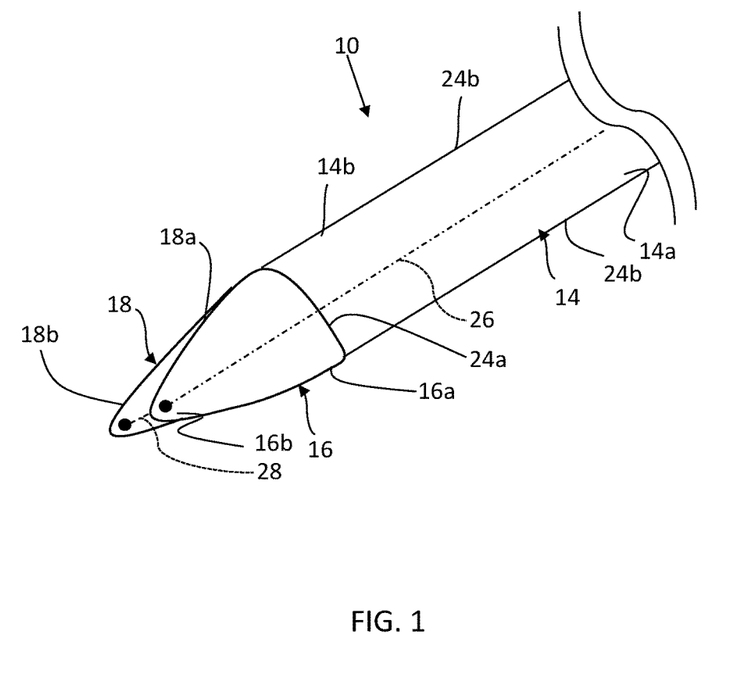
FIG. 1 is a partial perspective view illustrating an exemplary embodiment of a cannula.
Figure 2:
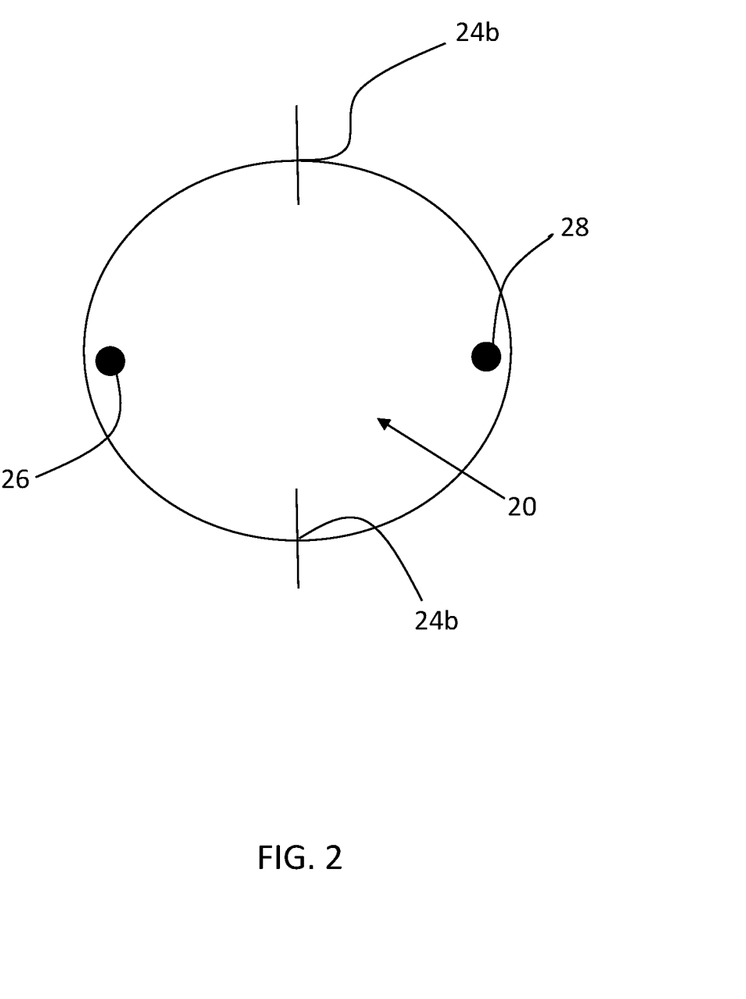
FIG. 2 is a transverse cross-sectional view illustrating the cannula of FIG. 1.
Figure 3:
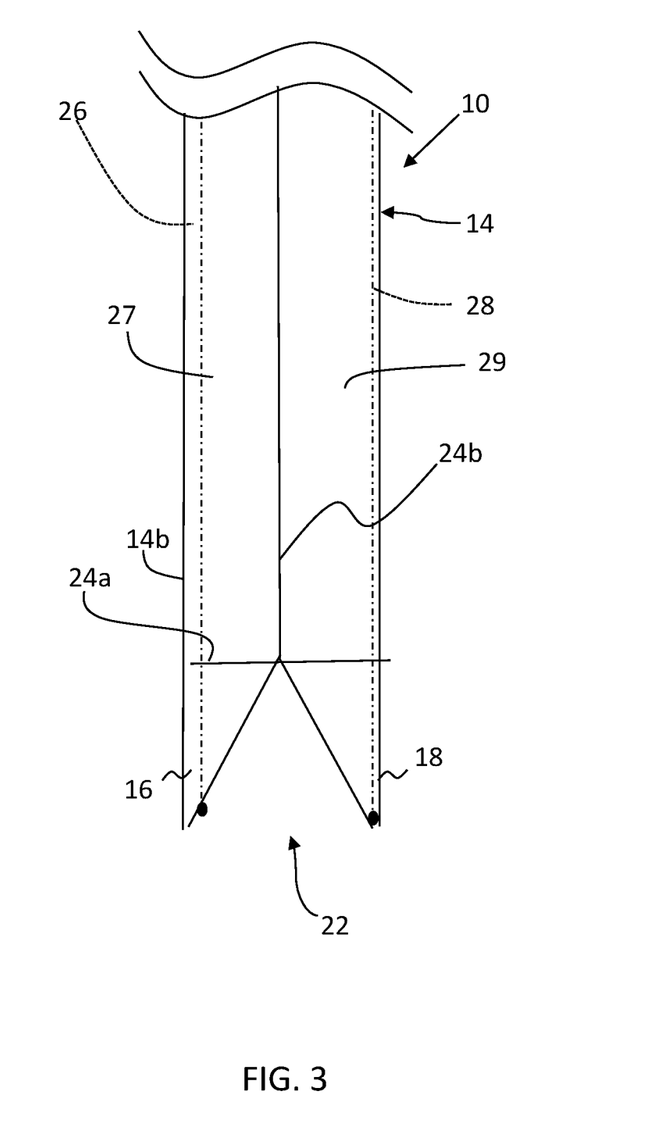
FIG. 3 is a partial side view, with parts shown in phantom, illustrating the cannula of FIG. 1.
Figure 4:
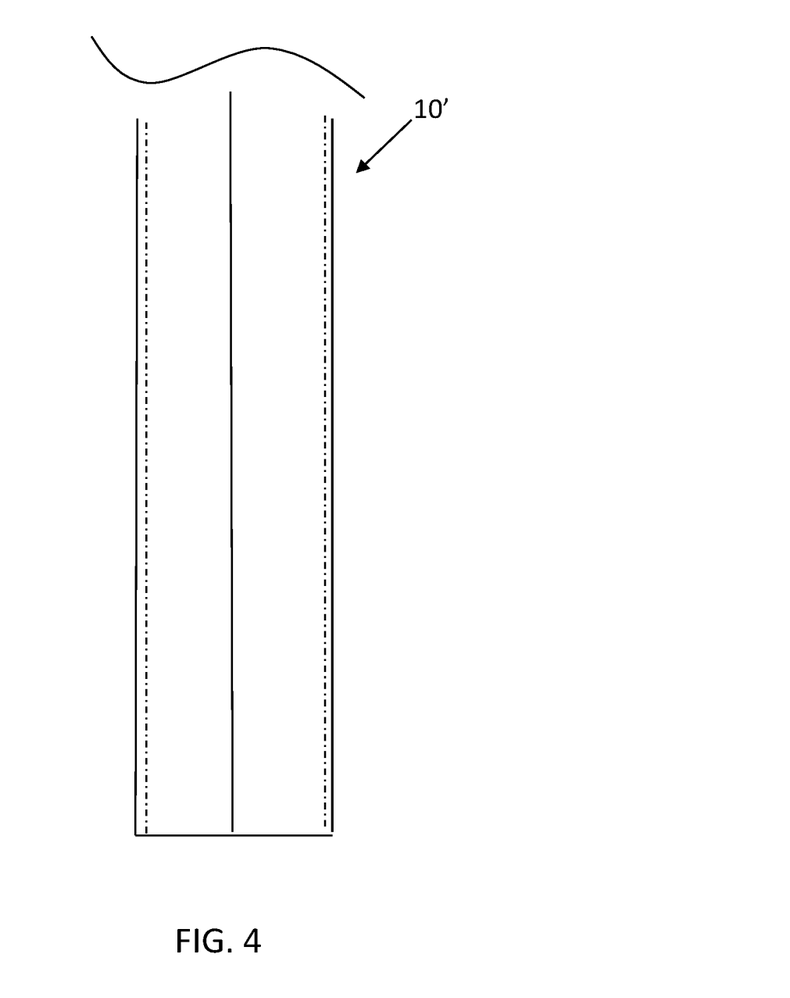
FIG. 4 is a longitudinal cross-sectional view illustrating another embodiment of a cannula.

FIGS. 1-3 illustrate an exemplary embodiment of a cannula 10 for performing a biopsy or for providing access to a surgical site. The cannula 10 generally includes a an elongate body portion, such as, for example, a tubular shaft 14, a handle portion (not explicitly shown) coupled to a proximal end portion 14a of the tubular shaft 14, and first and second distal extensions 16, 18 coupled to a distal end portion 14b of the tubular shaft 14. In aspects, a cannula may be provided that is devoid of the distal extensions 16, 18 and instead has a cylindrical configuration throughout its length, such as the cannula 10' shown in FIG. 4. The tubular shaft 14 defines a longitudinally-extending passageway 20 and is fabricated from any suitable material including a metal or plastic, such as, for example, silicone rubber, polyurethane, PET, thermoplastic polymers, and/or nylon. In aspects, the tubular shaft 14 and the first and second distal extensions 16, 18 may be fabricated from thin, high temperature plastics, such as, for example, polyetheretherketone, polyetherimide, polysulfone, and/or polyvinylidene fluoride. As such, the distal end portion 14b of the tubular shaft 14 may be peelable or bendable.

The distal extensions 16, 18 of the cannula 10 extend distally from the distal end portion 14b of the tubular shaft 14. In aspects, the distal extensions 16, 18 may be monolithically formed with the distal end portion 14b of the tubular shaft 14 or be connected thereto in any other suitable manner, e.g., via mechanical engagement, adhesion, etc. The distal extensions 16, 18 may each have a generally triangular configuration and define a triangular space or cutout 22 therebetween to assist in bending the distal extensions 16, 18 inwardly to initiate a tear of the cannula 10, as will be described. The distal extensions 16, 18 each have a proximal end 16a, 18a attached to the distal end portion 14b of the tubular shaft 14. In aspects, the proximal end 16a, 18a of the distal extensions 16, 18 may be attached to the distal end portion 14b of the tubular shaft via a frangible connection 24a.

The frangible connection 24a has a reduced thickness compared to a thickness of the distal end portion 14b of the tubular shaft 14, such that the distal extensions 16, 18 are more likely to separate or break from the distal end portion 14b at the frangible connection 24a. The frangible connection 24a may be a groove that extends circumferentially about the distal end portion 14b of the tubular shaft 14 at a location where the proximal ends 16a, 18a of the distal extensions 16, 18 connect to the tubular shaft 14. The groove 24a may be formed by scoring the tubular shaft 14. In other aspects, the frangible connection 24a may include perforations.

With continued reference to FIGS. 1-3, the cannula 10 may include another frangible connection, such as, for example, a pair of second grooves 24b disposed on opposite sides of the tubular shaft 14 and extending parallel with a longitudinal axis defined by the tubular shaft 14. The grooves 24b are disposed between the proximal end 16a of the first distal extension 16 and the proximal end 18a of the second distal extension 18 and bisect the tubular shaft 14 into two longitudinal half-sections 27, 29. The grooves 24b may extend a length of at least about 3-6 cm, and in aspects about 4 cm, proximally from a distal-most end of the tubular shaft 14. The grooves 24b may be formed by having a reduced thickness at the location of the grooves 24b or by scoring to facilitate tearing or peeling of the two longitudinal half-sections 27, 29 of the tubular shaft 14 about the grooves 24b. In other aspects, first and second strips of weaker material may be used to attach the two longitudinal sections 27, 29 of the tubular shaft 14.

The cannula 10 further includes first and second tethers 26, 28. The first and second tethers 26, 28 are coupled to the respective distal ends 16b, 18b of the first and second distal extensions 16, 18. In aspects, only one tether 26 or 28 may be provided that couples to both of the first and second distal extensions 16, 18. The tethers 26, 28 extend proximally through the cannula 10 and terminate in a proximal end (not explicitly shown) that may be manipulated by a clinician.

In some aspects, the distal extensions 16, 18 may be slidably coupled to the distal end portion 14b, such that the distal extensions 16, 18 may be axially translated between extended and retracted states.

In operation, the cannula 10 may be inserted through a natural or artificial tissue opening and guided to a target tissue site. In some aspects, the cannula 10 may be passed through a working channel of an endoscope or other access-providing device and/or may be guided along a stylet to the surgical site. The distal extensions 16, 18 of the cannula 10 are positioned within or adjacent a tumor and are used to either gather a sample of the tumor or to guide another surgical instrument (e.g., an electrosurgical instrument) to the tumor.

After using the cannula 10, but prior to withdrawing the cannula 10 from the surgical site, a proximally-oriented force is applied to the tethers 26, 28 sufficient to break, bend, peel, or tear the distal extensions 16, 18 from the tubular shaft 14 at the first groove 24a. During breaking or bending, the distal ends 16b, 18b of the distal extensions 16, 18 pivot inwardly toward one another about the groove 24a. A further proximally-oriented force exerted on the tethers 26, 28 folds the distal ends 16b, 18b of the distal extensions 16, 18 inwardly and proximally while also tearing or peeling the distal end portion 14b of the tubular shaft 14 about the second grooves 24b, thereby everting the distal extensions 16, 18 and the distal end portion 14b of the tubular shaft within the passageway 20 of the tubular shaft 14. In this way, a generally distal region of the cannula 10 is turned inside out.

With the distal extensions 16, 18 and the distal end portion 14b of the tubular shaft 14 folded inside out, the cannula 10 may be withdrawn from the surgical site. Since the distal extensions 16, 18 and/or distal end portion 14b of the tubular shaft 14 are the only portions of the cannula 10 to have potentially made contact with the tumor and now have their outer surfaces inside of the tubular shaft 14, withdrawal of the cannula 10 from the surgical site will not pose any risk of tract seeding.

Figure 5:
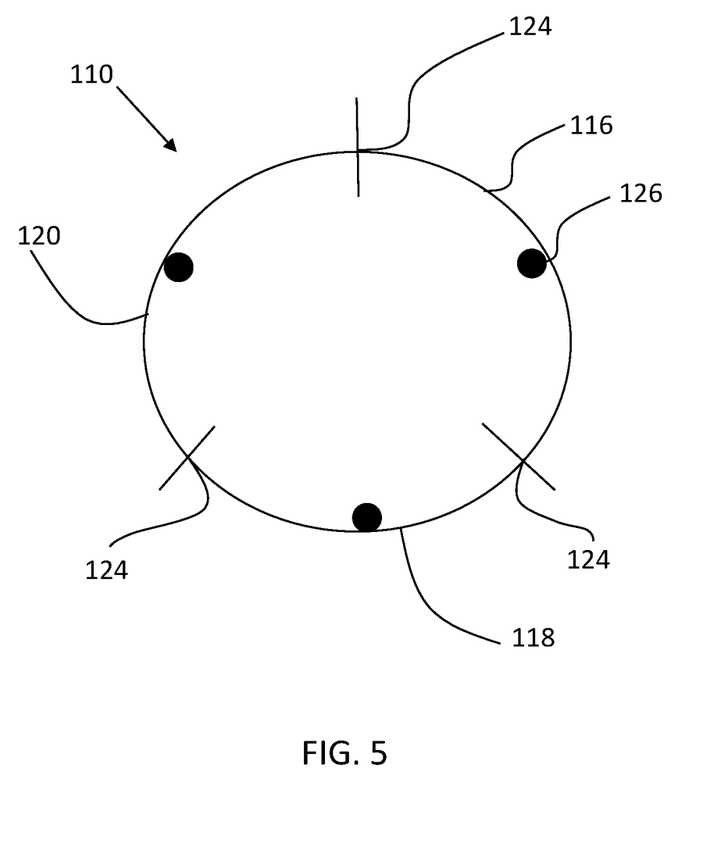
FIG. 5 is a transverse cross-sectional view illustrating another embodiment of a cannula.
Figure 6:
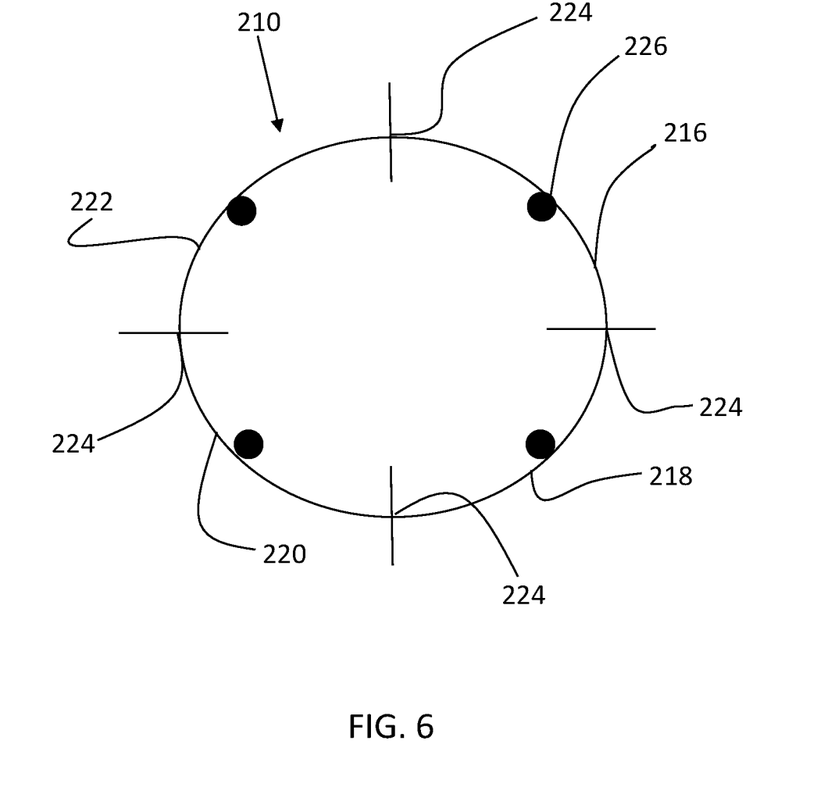
FIG. 6 is a transverse cross-sectional view illustrating yet another embodiment of a cannula.

FIGS. 5 and 6 illustrate additional embodiments of a cannula 110 and 210, similar to the cannula 10 of FIGS. 1-4. The cannula 110 has three longitudinal sections 116, 118, 120 formed by three vertically-extending grooves 124, and three tethers 126 attached to respective distal ends of the longitudinal sections 116, 118, 120. The cannula 210 has four longitudinal sections 216, 218, 220, 22 formed by four vertically-extending grooves 224, and four tethers 226 attached to respective distal ends of the longitudinal sections 216, 218, 220, 22.

It is contemplated that the cannula disclosed herein may have any suitable number of longitudinal sections and grooves for facilitating separation of the longitudinal sections.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques).

What is claimed is:

1. A cannula for use in a surgical procedure, the cannula comprising:
    a tubular shaft having a distal end portion and defining a longitudinal passageway;
    a first groove extending longitudinally along the distal end portion of the tubular shaft;
    a pair of laterally-spaced distal extensions attached to the distal end portion of the tubular shaft by a frangible connection; and
    at least one tether coupled to the pair of laterally-spaced distal extensions, the distal end portion configured to break or bend about the first groove in response to a threshold proximally-oriented force applied to the at least one tether, wherein the proximally-oriented force pivots the pair of laterally-spaced distal extensions inwardly toward each other to separate the pair of distal extensions from the tubular shaft at the frangible connection and everts the pair of laterally-spaced distal extensions into the longitudinal passageway of the tubular shaft.

2. The cannula according to claim 1, wherein the at least one tether includes a first tether coupled to a first distal extension of the pair of laterally-spaced distal extensions and a second tether coupled to a second distal extension of the pair of laterally-spaced distal extensions.

3. The cannula according to claim 1, wherein the tubular shaft is fabricated from a plastic.

4. The cannula according to claim 3, wherein the plastic is a high temperature plastic.

5. The cannula according to claim 3, wherein the plastic is selected from the group consisting of polyetheretherketone, polyetherimide, polysulfone, and polyvinylidene fluoride.

6. The cannula according to claim 1, wherein the frangible connection includes a second groove defined circumferentially about the distal end portion of the tubular shaft.

7. The cannula according to claim 1, wherein the first groove extends parallel with a longitudinal axis defined by the tubular shaft.

8. The cannula according to claim 1, wherein the first groove is a pair of grooves disposed on opposite sides of the distal end portion of the tubular shaft.

9. The cannula according to claim 8, wherein the distal end portion of the tubular shaft includes a first longitudinal section and a second longitudinal section, the first and second longitudinal sections configured to separate from one another about the pair of grooves and fold inwardly.

10. The cannula according to claim 1, wherein the proximally-oriented force is configured to evert the distal end portion of the tubular shaft into the longitudinal passageway of the tubular shaft.

11. A cannula for use in a surgical procedure, the cannula comprising:

a tubular shaft defining a longitudinal passageway and including a first groove formed longitudinally along a surface of the tubular shaft;

a pair of laterally-spaced distal extensions attached to a distal-most end of the tubular shaft at a second groove formed circumferentially around the tubular shaft; and at least one tether coupled to the pair of laterally-spaced distal extensions, wherein in response to a proximally-oriented force applied to the at least one tether the pair of laterally-spaced distal extensions are configured to pivot inwardly toward each other to separate the pair of distal extensions from the distal-most end of the tubular shaft at the second groove and at least a portion of the tubular shaft is configured to tear along the first groove.

12. The cannula according to claim 11, wherein application of the proximally-oriented force is configured to evert the pair of laterally-spaced distal extensions into the longitudinal passageway of the tubular shaft.

13. The cannula according to claim 11, wherein application of the proximally-oriented force is configured to evert a distal end portion of the tubular shaft into the longitudinal passageway of the tubular shaft.

* * * * *